(12) United States Patent
     Butler

(10) Patent No.:     US 12,194,306 B2
(45) Date of Patent:     Jan. 14, 2025

(54) PORTABLE DEFIBRILLATOR USED FOR DISPLAY, HARDCOPY, AND CONTROL FOR OTHER DEVICES

(71) Applicant: ZOLL Medical Corporation, Chelmsford, MA (US)

(72) Inventor: Gideon D. H. Butler, Portsmouth, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 451 days.

(21) Appl. No.: 17/643,860

(22) Filed: Dec. 13, 2021

(65) Prior Publication Data

US 2022/0241602 A1    Aug. 4, 2022

Related U.S. Application Data

(63) Continuation of application No. 16/507,339, filed on Jul. 10, 2019, now Pat. No. 11,241,583, which is a continuation of application No. 16/150,504, filed on Oct. 3, 2018, now Pat. No. 10,391,326, which is a continuation of application No. 14/498,889, filed on Sep. 26, 2014, now Pat. No. 10,124,185.

(60) Provisional application No. 61/883,779, filed on Sep. 27, 2013.

(51) Int. Cl.
    *A61N 1/39*      (2006.01)
    *A61B 8/00*      (2006.01)
    *G06F 9/455*     (2018.01)

(52) U.S. Cl.
    CPC .............. *A61N 1/3993* (2013.01); *A61B 8/44* (2013.01); *A61B 8/56* (2013.01); *G06F 9/45533* (2013.01)

(58) Field of Classification Search
    CPC ................................ A61N 1/3993; A61B 8/44
    USPC ............................................................ 607/6
    See application file for complete search history.

(56) References Cited

U.S. PATENT DOCUMENTS

| 4,974,600 | A  | 12/1990 | Reyes        |
|-----------|----|---------|--------------|
| 5,199,429 | A  | 4/1993  | Kroll et al. |
| 5,247,945 | A  | 9/1993  | Heinze et al.|
| 5,441,518 | A  | 8/1995  | Adams et al. |
| 5,507,781 | A  | 4/1996  | Kroll et al. |
| 5,709,710 | A  | 1/1998  | Armstrong    |
| 6,259,941 | B1 | 7/2001  | Chia et al.  |
| 6,336,047 | B1 | 1/2002  | Thu et al.   |
| 6,556,865 | B2 | 4/2003  | Walcott et al.|

(Continued)

*Primary Examiner* — Nadia A Mahmood
(74) *Attorney, Agent, or Firm* — Finch & Maloney PLLC

(57) ABSTRACT

A shared resource medical system for monitoring a patient during emergency situations includes a primary medical device including a processor configured to wirelessly receive and transmit data, at least one secondary medical device communicatively coupled to the primary medical device and configured to collect physiological information from a patient, and transmit the physiological information to the primary medical device, and a remote computing device disposed at a location remote from the primary medical device and the at least one secondary medical device, wherein the primary medical device is configured to receive the physiological information from the at least one secondary medical device, and transmit the physiological information to the remote computing device, and wherein the remote computing device is configured to monitor the physiological information collected by the at least one secondary medical device.

20 Claims, 11 Drawing Sheets

(56) References Cited

U.S. PATENT DOCUMENTS

| | | |
|---|---|---|
| 6,687,541 B2 | 2/2004 | Marcovecchio et al. |
| 6,690,958 B1 | 2/2004 | Walker et al. |
| 6,760,621 B2 | 7/2004 | Walcott et al. |
| 7,006,865 B1* | 2/2006 | Cohen ............... A61N 1/3904 607/5 |
| 7,079,894 B2 | 7/2006 | Lyster et al. |
| 7,650,181 B2 | 1/2010 | Freeman et al. |
| 7,699,778 B2 | 4/2010 | Adam |
| 7,751,881 B2 | 7/2010 | Cowan et al. |
| 7,899,537 B1 | 3/2011 | Kroll et al. |
| 7,962,207 B2 | 6/2011 | Nassif |
| 8,038,617 B2 | 10/2011 | Maschke |
| 8,077,944 B2 | 12/2011 | Schummers |
| 8,135,462 B2 | 3/2012 | Owen et al. |
| 8,160,698 B2 | 4/2012 | Elghazzawi et al. |
| 8,532,766 B2 | 9/2013 | Joo et al. |
| 8,591,425 B2 | 11/2013 | Owen et al. |
| 8,663,121 B2 | 3/2014 | Stickney et al. |
| 8,731,658 B2 | 5/2014 | Hampton et al. |
| 8,744,577 B2 | 6/2014 | Joo et al. |
| 9,028,417 B2 | 5/2015 | Sverdlik et al. |
| 9,174,061 B2 | 11/2015 | Freeman et al. |
| 9,289,621 B2 | 3/2016 | Aoyama et al. |
| 9,457,197 B2 | 10/2016 | Aoyama et al. |
| 2004/0162510 A1 | 8/2004 | Jayne et al. |
| 2005/0033385 A1 | 2/2005 | Peterson et al. |
| 2005/0065557 A1 | 3/2005 | Powers et al. |
| 2005/0107833 A1 | 5/2005 | Freeman et al. |
| 2007/0150024 A1* | 6/2007 | Leyde ............... A61N 1/37258 607/45 |
| 2007/0184085 A1 | 8/2007 | Radhakrishnan et al. |
| 2008/0086175 A1 | 4/2008 | Libbus et al. |
| 2008/0294210 A1 | 11/2008 | Rosero |
| 2009/0149901 A1* | 6/2009 | Jayne ................. A61H 31/006 601/41 |
| 2009/0306525 A1 | 12/2009 | Pinter et al. |
| 2009/0318808 A1 | 12/2009 | Brader |
| 2010/0094149 A1 | 4/2010 | Kohut et al. |
| 2012/0123223 A1* | 5/2012 | Freeman ............ A61B 5/0002 600/509 |
| 2012/0136404 A1* | 5/2012 | Drew ................. A61N 1/3993 607/6 |
| 2012/0158074 A1 | 6/2012 | Hall |
| 2013/0304142 A1 | 11/2013 | Curtin et al. |
| 2013/0304146 A1 | 11/2013 | Aoyama et al. |

\* cited by examiner

PORTABLE DEFIBRILLATOR USED FOR DISPLAY, HARDCOPY, AND CONTROL FOR OTHER DEVICES

CROSS-REFERENCE TO RELATED APPLICATION

This is a continuation of U.S. patent application Ser. No. 16/507,339 (filed 10 Jul. 2019 now U.S. Pat. No. 11,241,583), which is a continuation of U.S. patent application Ser. No. 16/150,504 (filed 3 Oct. 2018, now U.S. Pat. No. 10,391,326), which is a continuation of U.S. patent application Ser. No. 14/498,889 (filed 26 Sep. 2014, now U.S. Pat. No. 10,124,185), which claims the benefit of U.S. Provisional Patent Application 61/883,779 (filed 27 Sep. 2013). U.S. Provisional Patent Application 61/883,779 which is incorporated herein by reference in its entirety for all purposes.

TECHNICAL FIELD

Embodiments of the present invention generally relate to medical devices and, in particular, relate to improved medical devices for emergency scenarios.

BACKGROUND

Medical services are required in many emergency situations. To provide those medical services, trained personnel, such as paramedics, use medical equipment, such as defibrillators, when responding to medical needs in emergency situations. At the same time, emergency situations often occur away from locations directly accessible by an ambulance. For example, paramedics may need to respond to a medical emergency in an apartment or office at the top of a skyscraper. In those situations, paramedics must carry the medical equipment with them. The complexities of many emergency situations and the potentially unknown medical requirements of persons in those emergency situations can require the paramedics to transport a variety of medical equipment. This can overburden and slow down the paramedics, costing precious time that is needed to save lives.

SUMMARY

According to some embodiments of the present invention, multiple medical devices share resources in order to decrease the amount of equipment needed to respond to medical emergencies. For example, a portable defibrillator is equipped with a screen and operates to collect and display defibrillator information on its screen. The portable defibrillator also connects with a medical device, such as an ultrasound transducer, and collects and displays ultrasound information using that same screen. In some embodiments, one or more independent virtual machines operate on the portable defibrillator. The portable defibrillator performs defibrillator functions and one of the virtual machines performs ultrasound operations. The portable defibrillator may serve as a virtual machine host that is able to override or shut down the virtual machine performing ultrasound operations based on user input, detection of an error condition, or detection of an alarm condition. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

In emergency situations, paramedics are asked to perform emergency medical services for injured individuals. In order to address a variety of medical situations, paramedics often need a variety of medical devices. For example, portable defibrillators are used to treat cardiac dysrhythmia and/or to monitor cardiac conditions using ECG leads. For another example, ultrasound machines are used to provide diagnostic images and/or ultrasonic treatment to patients. Other exemplary medical devices used by paramedics include: ventilators, oximeters, blood pressure monitors, and/or the like. In addition, paramedics also use non-medical equipment, such as GPS devices, to precisely locate emergencies. While paramedics frequently require multiple devices in any given emergency, carrying and using each piece of equipment separately is cumbersome and can lead to wasted time—a precious commodity in medical emergencies.

According to embodiments of the present invention, the medical devices are modified in order to share resources, such as display screens, printers, controls, wireless connections, etc., in order to reduce the amount of equipment that a paramedic must carry. For example, a portable defibrillator, which already includes a screen for displaying cardiac information, may be modified to couple with an ultrasound transducer, process the physiological information provided by that transducer, and display the resulting image on the screen. Thus, rather than carrying and operating two complete medical devices, the paramedic can simply carry and operate the portable defibrillator with the ultrasonic transducer. Furthermore, in some embodiments, devices that share resources have reduced power requirements compared to two complete devices. As explained below in more detail, resources may be shared between multiple medical devices or between a medical device and a non-medical device, such as a GPS, further reducing the amount of equipment that the paramedic must carry and operate.

Figure 1:
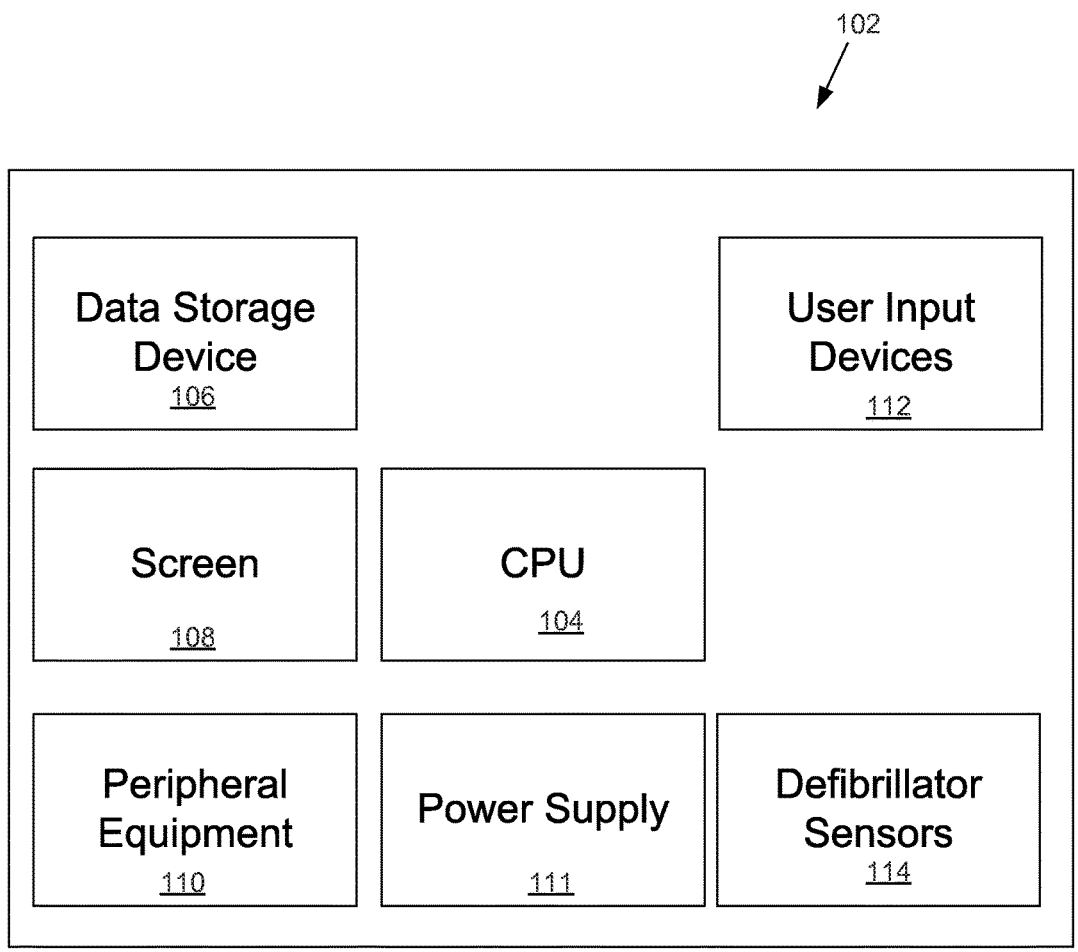
FIG. 1 depicts components of a portable defibrillator, according to embodiments of the present invention.

Referring now to FIG. 1, a portable defibrillator 102 includes a CPU 104 operatively coupled to a data storage device 106, a screen 108, peripheral equipment 110, and a power supply 111. Peripheral equipment 110 includes components such as a printer (for providing hardcopies of, for example, ECG or capnography stripcharts) and/or a wireless/cellular adapter. The power supply 111 may include an energy storage device (for example, a battery). The CPU 104 is also operatively coupled to user input devices 112, such as panel-mounted controls and/or a touchscreen, as well as defibrillator sensors 114. The portable defibrillator 102 may include additional components not depicted in FIG. 1, such as paddles, and may not have every component depicted in FIG. 1, such as the peripheral equipment 110. In one operational aspect, the defibrillator sensors 114 are attached to a patient and measure physiological data, which are sent to the CPU 104. The CPU 104 processes that data and presents the resulting physiological parameters to paramedics using the screen 108 and/or the peripheral equipment 110. The CPU 104 may also store the physiological parameters in the data storage device 106. Throughout this process, the paramedic may provide input via the user input devices 112.

Figure 2:
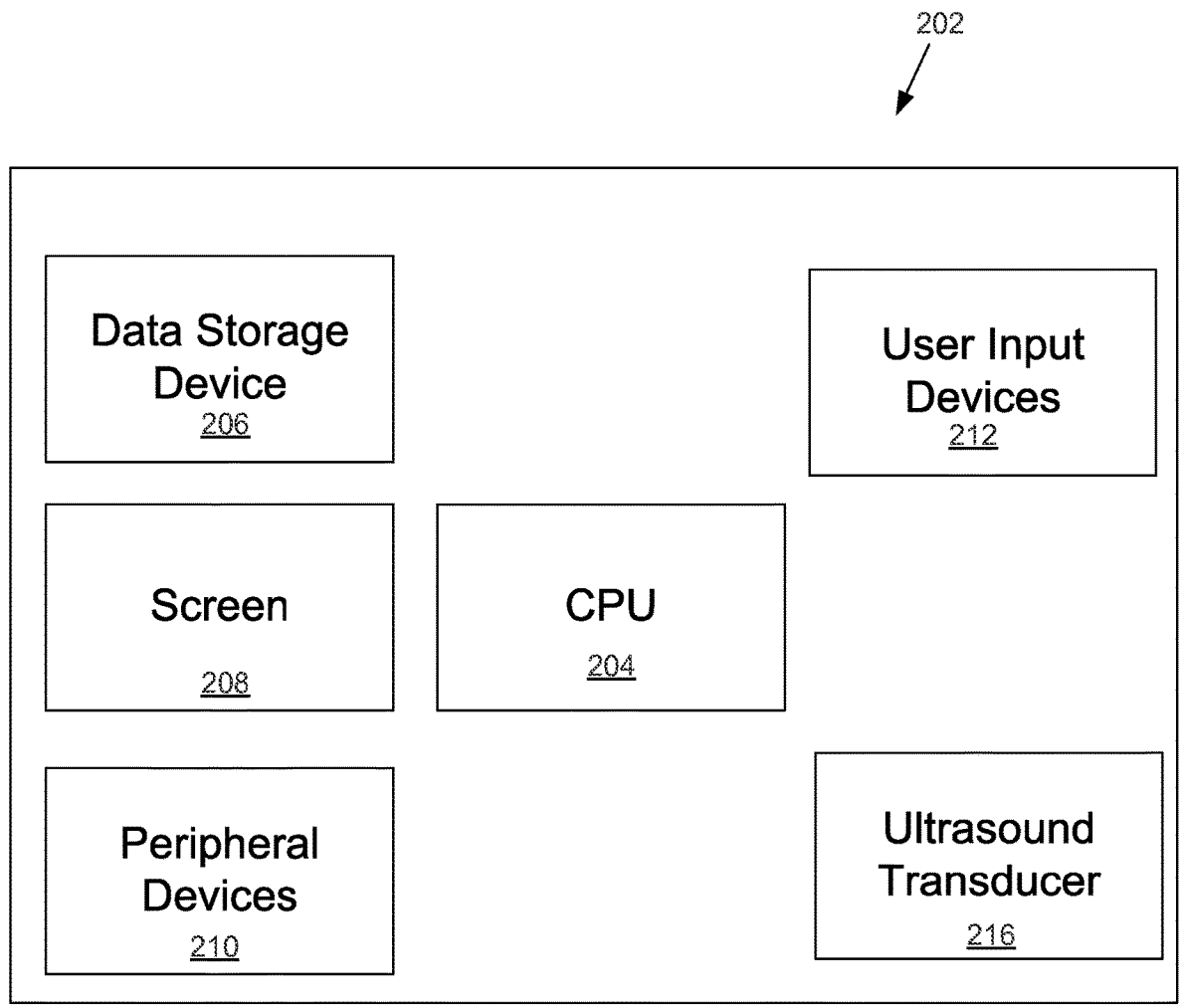
FIG. 2 depicts components of an ultrasound machine, according to embodiments of the present invention.

As shown in FIG. 2, an ultrasound machine 202 includes a CPU 204 operatively coupled to a storage device 206, a screen 208, and peripheral equipment 210. Peripheral equipment 210 includes components such as a printer (for providing hardcopies of, for example, ultrasound images). The CPU 204 is also operatively coupled to user input devices 212, such as a keyboard, mouse, and/or touchscreen, as well as an ultrasound transducer 216. The ultrasound machine 202 may include additional components not depicted in FIG. 2 and may not have every component depicted in FIG. 2. In one operational aspect, the ultrasound transducer 216 measures physiological data, which are sent to the CPU 204. The CPU 204 processes that data and presents the resulting physiological parameters (including, e.g., the ultrasonic image) to paramedics using the screen 208 and/or the peripheral equipment 210. The CPU 204 may also store the physiological parameters in the storage device 206. Throughout this process, the paramedic may provide input via the user input devices 212.

Thus, there is significant overlap between the resources used by the portable defibrillator 102 and the ultrasound machine 202, including, for example, the screen 108, 208. There is similar overlap for many medical and non-medical devices. By modifying the medical devices and non-medical devices to share resources, paramedics will be able to carry a lighter load and more quickly access needed functionalities. In addition, the medical devices and non-medical devices may have reduced power requirements by sharing resources. As discussed below in more detail, in some embodiments a medical device is modified to add functionalities associated with some other medical device without subtracting any of its existing functionalities. In those embodiments, the medical device is referred to as a primary device and the other medical device is referred to as a secondary device. For example, in the embodiments shown in FIG. 3, a portable defibrillator is the primary device and the ultrasound machine is the secondary device.

Figure 3:
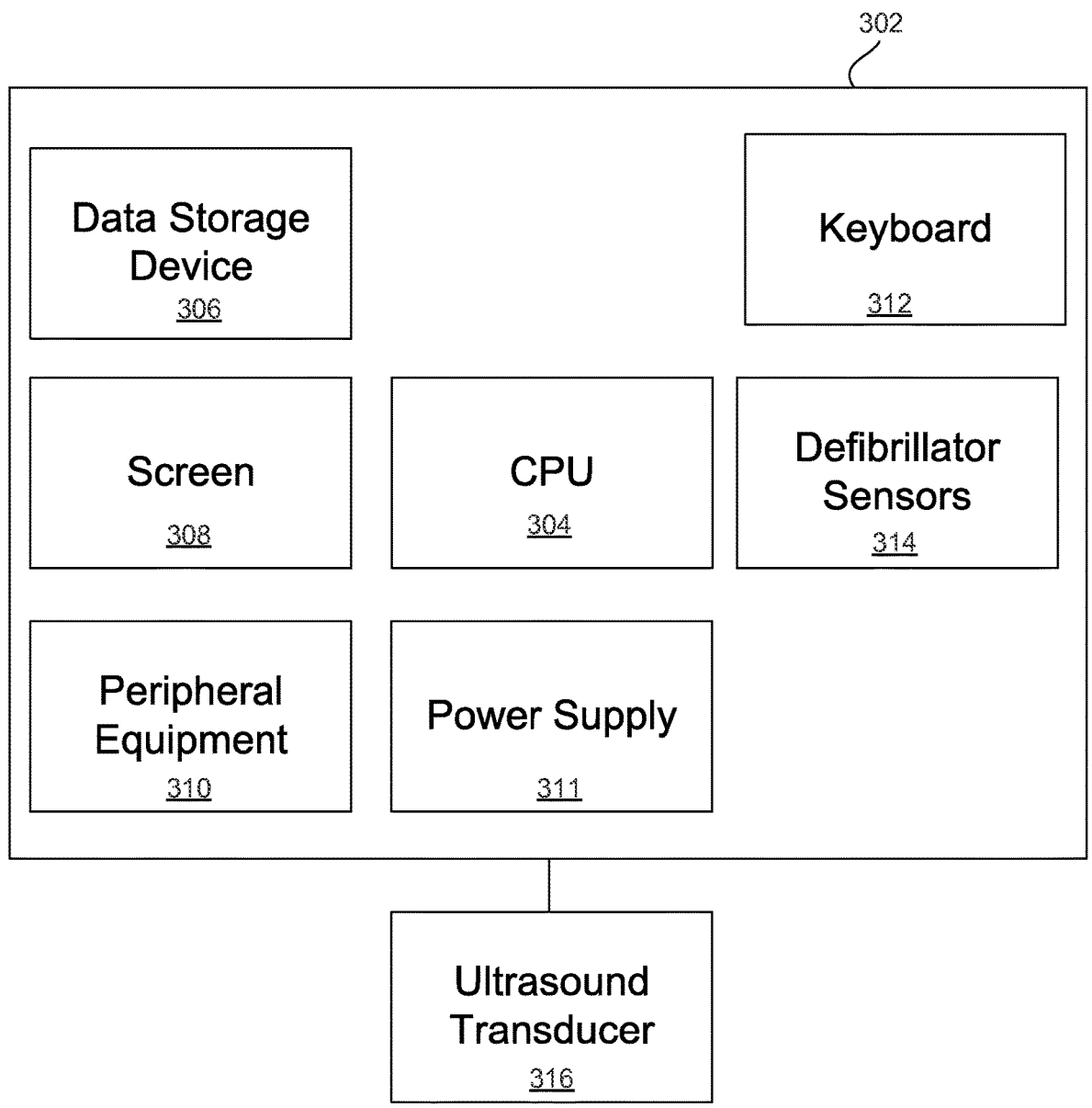
FIG. 3 depicts components of a portable defibrillator coupled with an ultrasound transducer, according to embodiments of the present invention.

Specifically, and as shown in FIG. 3, a portable defibrillator 302 includes a CPU 304 operatively coupled to a data storage device 306, a screen 308, peripheral equipment 310, such as a printer, and a power supply 311. The CPU 304 is also operatively coupled to user input devices 312, such as panel-mounted controls and/or a touchscreen, as well as defibrillator sensors 314 and an ultrasound transducer 316. The portable defibrillator 302 may include additional components not depicted in FIG. 3, such as paddles, and may not have every component depicted in FIG. 3, such as the peripheral equipment 310.

In some embodiments the ultrasound transducer 316 is physically coupled (i.e., tethered) to the portable defibrillator 302 via a cabled connection. In those embodiments, the ultrasound transducer 316 may receive power from the power supply 311. In other embodiments, the ultrasound transducer 316 and portable defibrillator 302 are configured to wirelessly communicate. In those embodiments, the ultrasound transducer 316 includes its own power supply. In those embodiments, the portable defibrillator 311 may provide an alarm if the power supply of the ultrasound transducer 316 is low or depleted. Additional security measures may be employed when connecting wirelessly. For example, a particular ultrasound transducer 316 may be assigned a particular identifier so that it will communicate with only a particular portable defibrillator 302. In this manner, multiple portable defibrillators and ultrasound transducers may be used in close proximity. Additional security features (e.g., encryption) may also be employed.

In one operational aspect, the defibrillator sensors 314 are attached to a patient and measure physiological data, which are sent to the CPU 304. The CPU 304 processes that data and presents the resulting physiological parameters to paramedics using the monitor 308. The CPU 304 may also store the physiological parameters in the data storage device 306. In another operational aspect, the ultrasound transducer 316 measures physiological data, which are sent to the CPU 304. The CPU 304 processes that data and presents the resulting physiological parameters (including, e.g., the ultrasonic image) to paramedics using the monitor 308. The CPU 304 may also store the physiological parameters in the data storage device 306. For example, the data storage device 306 may store an ultrasound image that provides a record of an endotracheal intubation procedure. Such a record would often not be captured or easily retrievable as would the patient encounter information stored in data storage device 306 by defibrillator 302, because such a record would normally be captured and/or stored only on the stand-alone ultrasound device. Instead, according to embodiments of the present invention, the ultrasound transducer 316 shares the defibrillator's 302 data storage device 306 resource, and the defibrillator 302 is configured to store such an ultrasound image associated with the particular patient encounter record to which it relates, so that it is easily accessible in later review of the disclosure data. In either operational aspect, the paramedic may provide input using the user input devices 312. Additional details regarding these operational aspects and their interactions are provided below.

As described above with respect to the example of an ultrasound image being stored by the defibrillator along with, and/or associated with, patient encounter information, the defibrillator 302 may similarly be configured to supplement its logging capabilities with information received from or generated about the secondary medical devices which are sharing one or more of its resources. This may include images, parameters, or any other data. Such data would normally be "trapped" on the secondary device or not stored at all, whereas embodiments of the present invention permit such data to be stored along with the patient record.

In some embodiments, the CPU 304 processes data received from the defibrillator sensors 314 and the ultrasound transducer 316 and presents the resulting physiological parameters using the peripheral equipment 310. If the peripheral equipment 310 includes a printer, for example, the physiological parameters may be presented as both ECG or capnography stripcharts and ultrasound images.

In some embodiments, the ultrasound transducer 316 includes only those components necessary to transmit ultrasonic sound pulses into the patient (for ultrasonic therapy). In other embodiments, the ultrasound transducer 316 includes only those components necessary to transmit ultrasonic sound pulses into the patient and to detect reflected sound pulses (for ultrasonic imaging). In yet other embodiments, the ultrasound transducer 316 includes its own CPU for processing the physiologic data into physiological parameters (e.g., the ultrasonic image), and the resulting physiological parameters are sent to the CPU 304 for presentation to the paramedics using the monitor 308 and/or the peripheral equipment 310. Thus, the amount of resources shared between devices may vary. Stated differently, the portable defibrillator 302 may incorporate most, if not all, of the data processing and other related features of the other medical device. As a result, only those components that physically interact with the patient and communicate measured parameters are required in order for the portable defibrillator 302 to provide all of the functionality of the other medical device.

While the embodiments provided above discuss a portable defibrillator that includes ultrasound functionalities, it should be noted that the invention is not limited to those two devices or their respective functionalities. Generally speaking, some embodiments of the invention use a portable defibrillator that includes functionalities for any number of medical or non-medical devices. Other embodiments use a different primary device (medical or non-medical) that incorporates functionalities from any number of secondary medical or non-medical devices.

Figure 4:
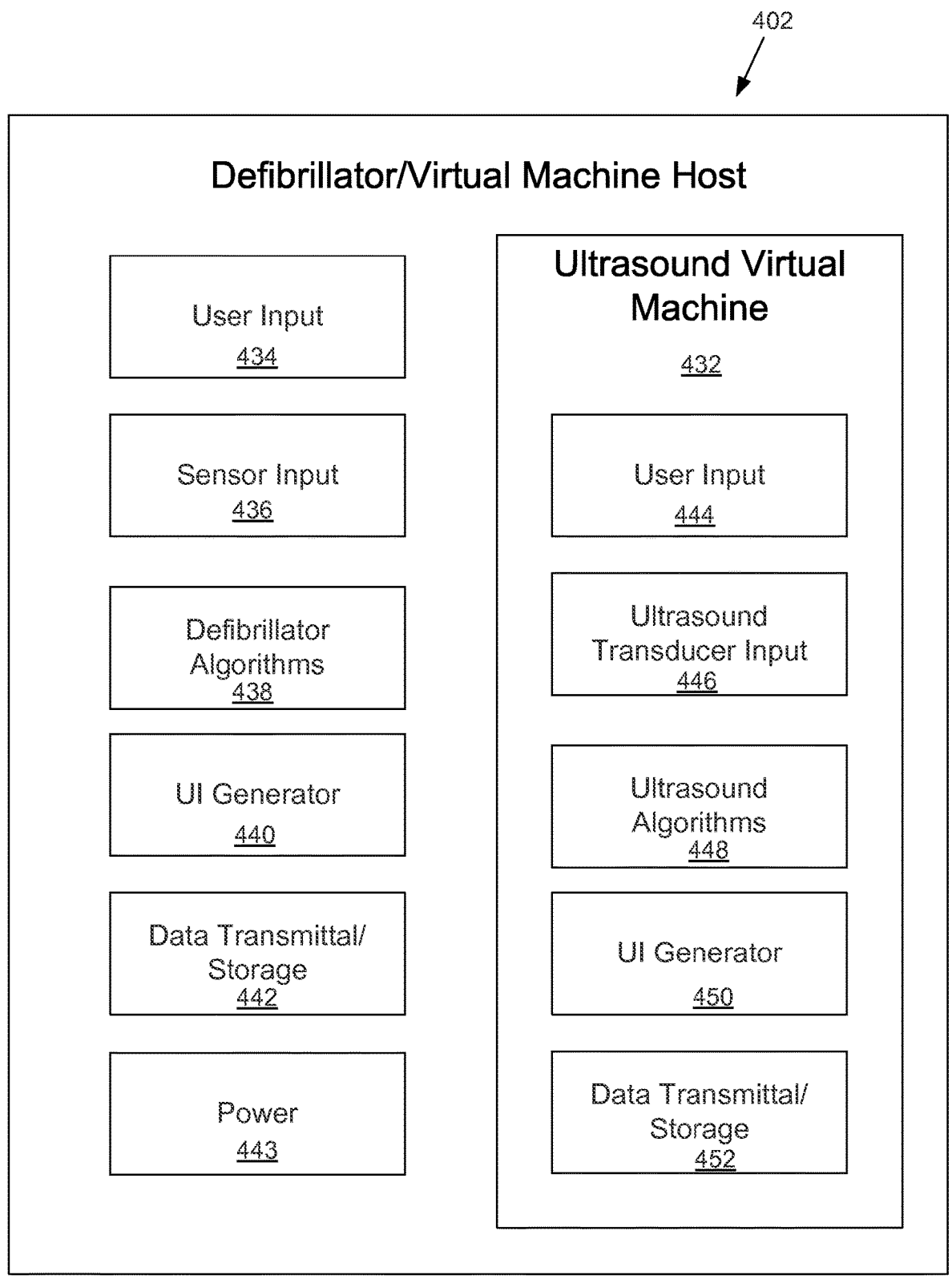
FIG. 4 depicts a virtual machine host and a virtual machine, as well as exemplary operating blocks for each machine, according to embodiments of the present invention.

In some embodiments, a medical device may act as a virtual machine host and operate one or more virtual machines. Each virtual machine corresponds to a particular medical device. For example, as shown in FIG. 4, a medical device 402 acts as a virtual machine host and includes one virtual machine 432 that corresponds to a particular medical device. While FIG. 4 depicts one virtual machine, in other embodiments the medical device 402 may include two, three, four, or five virtual machines, or may include more virtual machines.

In FIG. 4, the medical device 402 is a defibrillator machine that performs the functions of a defibrillator and acts as a virtual machine host. Virtual machine 432 is an ultrasound virtual machine 432 that performs the functions of an ultrasound machine. Specifically, in the embodiments shown in FIG. 4, the defibrillator machine 402 includes functional blocks for receiving and processing user input (block 434), receiving and processing sensor input (block 436), processing the input data to generate physiological parameters (block 438), generating a corresponding user interface for presenting the physiological parameters and/or soliciting user input (block 440), transmitting or storing the physiological parameters (block 442), and providing power to the medical device (block 443). Similarly, the ultrasound virtual machine 432 includes functional blocks for receiving and processing user input (block 444), receiving and processing transducer input (block 446), processing the input data to generate physiological parameters (block 448), generating a corresponding user interface for presenting the physiological parameters and/or soliciting user input (block 450), and transmitting or storing the physiological parameters (block 452).

Figure 5:
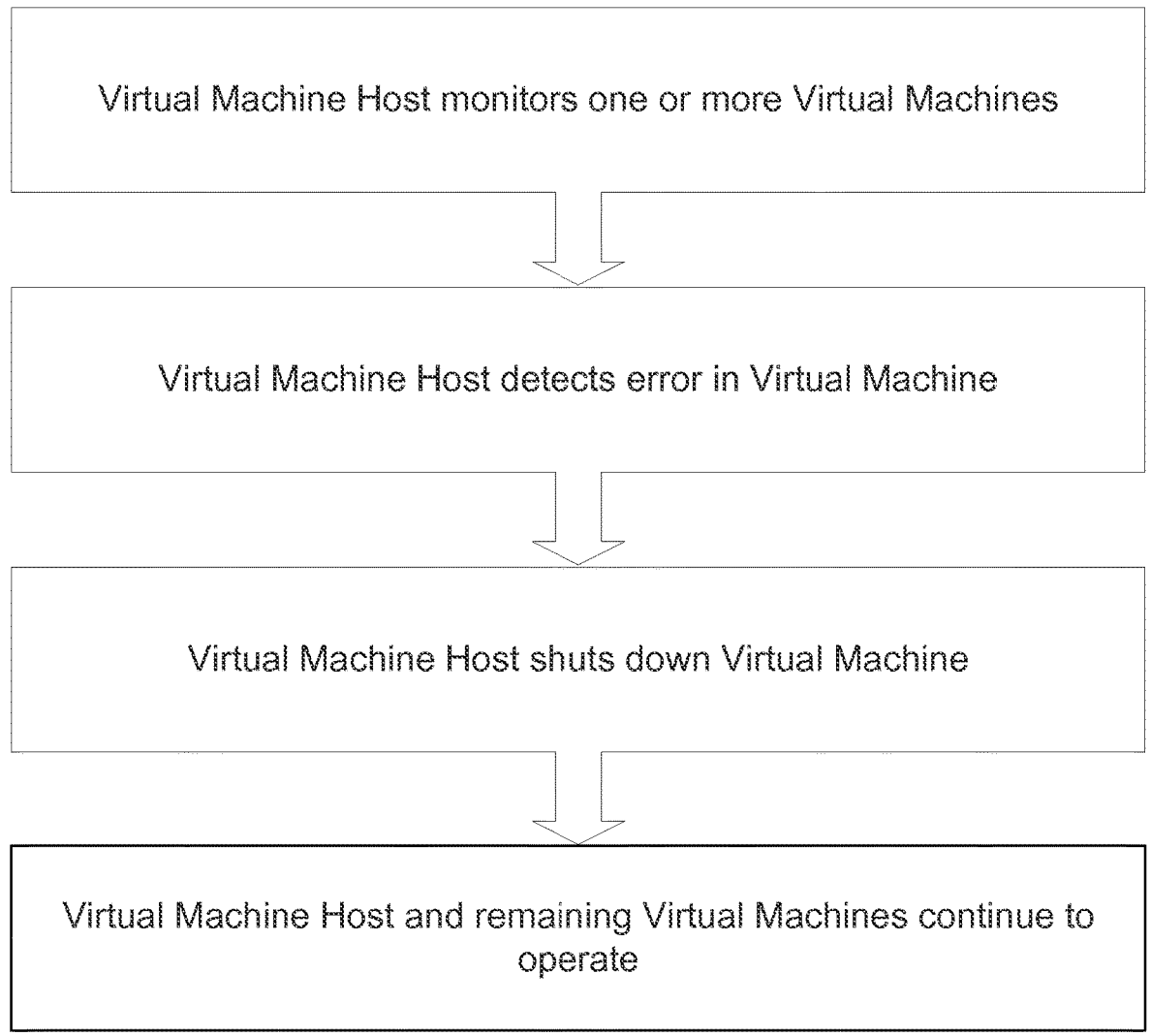
FIG. 5 depicts steps taken by a virtual machine host to shut down a virtual machine, according to embodiments of the present invention.

In some embodiments, the virtual machine host 402 may perform the functions of a medical device or may be solely tasked with supervising one or more virtual machines. In either case, the virtual machine host 402 is able to monitor the operations of the virtual machines and interrupt or shut down some or all of the virtual machines. For example and as shown in FIG. 5, the virtual machine host 402 monitors the virtual machines to detect any error conditions within those virtual machines. The error conditions may include internal errors, such as registry errors, faulty components, segmentation faults, and/or the like. The ability to shut down malfunctioning virtual machines allows the medical device 402 and the remaining virtual machines to continue to operate, so that paramedics are not denied access to critical functions in emergency situations.

The virtual machine host 402, in some embodiments, may also monitor alarm conditions from one or more virtual machines. As described below in more detail, the screen of a primary device, e.g., a portable defibrillator, may be used to display physiological parameters from a virtual machine. Meanwhile, the remaining virtual machines (and, in some embodiments, the virtual machine host 402) continue to process data and generate physiological parameters. If any of those parameters exceed an alarm threshold, the virtual machine host 402 will detect the alarm condition and will automatically instruct the corresponding virtual machine to display its physiological parameters, including the alarming condition, according to embodiments of the present invention. In this manner, paramedics can be quickly apprised of alarming conditions without needing to search through all the possible virtual machines. In the same fashion, when a user is viewing in a primary display information which is not critical to patient care from or about the virtual machine, and the virtual machine host 402 (for example, a defibrillator) detects a certain condition, it may be configured to replace the primary display information with information that has been obtained or determined by its sensor input 436 and/or algorithms 438 in order to provide the information which the paramedic needs most for patient care at that particular time. For example, if the primary display of a defibrillator device is being used to perform an ultrasound operation with a communication link between the defibrillator and the ultrasound device, and if the patient enters cardiac arrest, the defibrillator may be configured to automatically override the primary display in order to display the patient information from the defibrillator.

FIGS. 6-11 depict a modified medical device 602, such as a portable defibrillator, that uses a variety of user interfaces in order to communicate information with and receive input from paramedics. For example, FIGS. 6-11 depict a defibrillator user interface 604, an ultrasound user interface 704, a joint user interface 804, a GPS user interface 904, an endoscopy user interface 1004, and an electroencephalography (EEG) user interface 1104, respectively. In some embodiments, the user interfaces 604, 704, 804, 904, 1004, and 1104 have common components, such as soft buttons 606-610. These soft buttons 606-610 may be selected through user input means, such as panel mounted controls or a touch screen. The predetermined functions associated with each of the soft buttons 606-610 may change depending on the particular user interface operated by a particular virtual machine. The medical device 602 may also include hard buttons 612-616, which are each associated with predetermined functions. In this regard, the user interfaces 604, 704, 804, 904, 1004, and 1104 can emulate or mimic the user interface originally provided on the secondary device, with the number of soft buttons changing to match what is provided in the original user interface. The predetermined functions associated with each of the hard buttons 612-616 may change depending on the particular user interface operated by a particular virtual machine, or the predetermined functions may be the same for all virtual machines. For example, hard button 612 may always be associated with a "home" function that will instruct medical device 602 to display a home screen or a "home" user interface (e.g., the defibrillator user interface 604). In some embodiments, the functions associated with soft buttons 606-610 and/or hard buttons 612-616 are not predetermined but may be assigned on the fly by the paramedics.

Figure 6:
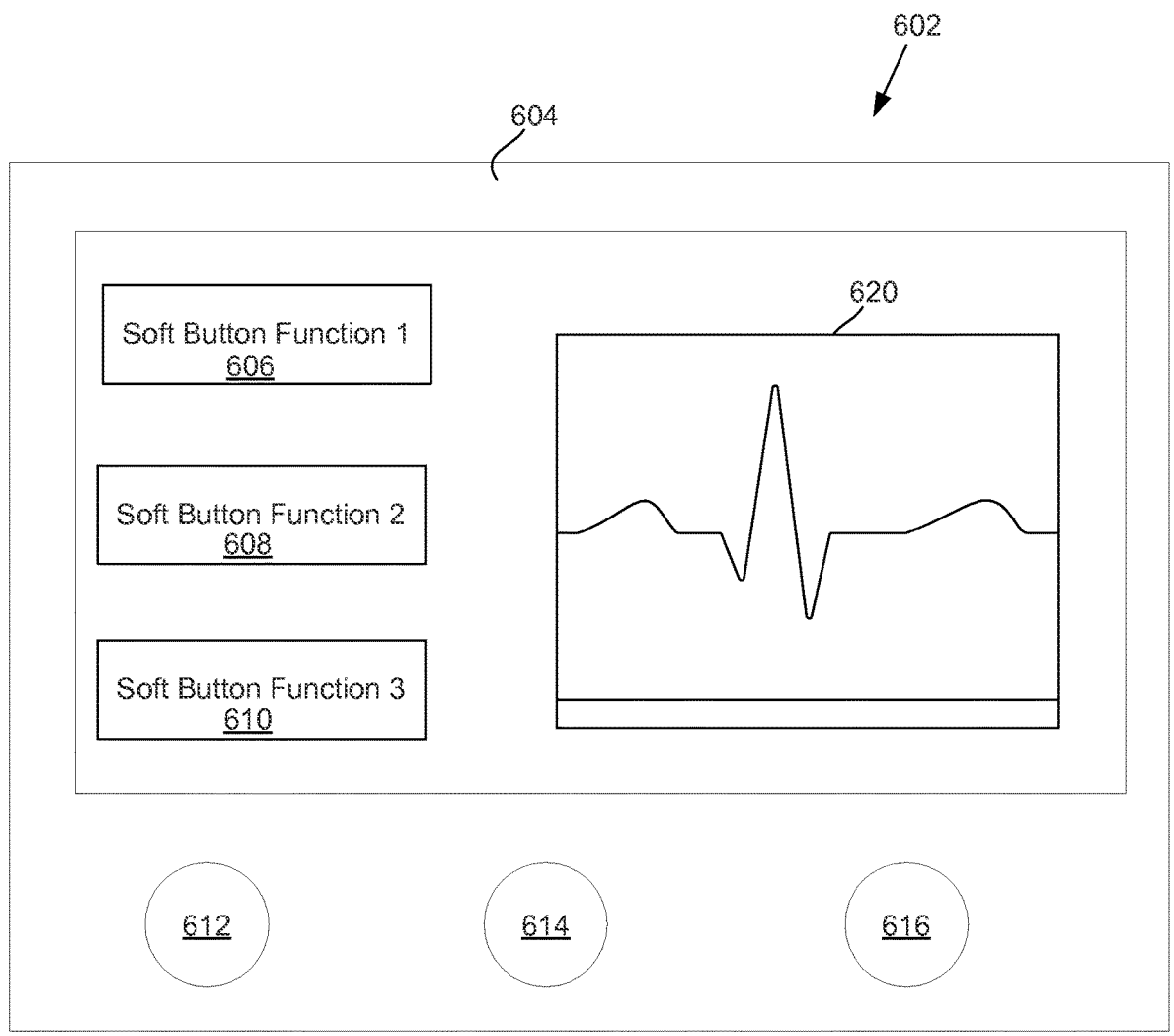
FIG. 6 illustrates a user interface of the portable defibrillator of FIG. 3 when operating in the defibrillator mode.

Referring now to FIG. 6, the defibrillator user interface 604 includes a parameter window 620 in which the defibrillator information, including physiological parameters (for example, an ECG waveform), may be displayed in chart form. The defibrillator user interface 604 includes soft buttons 606-610, which are each associated with predetermined functions, such as cycle display, zoom in/out, print, save, and the like.

Figure 7:
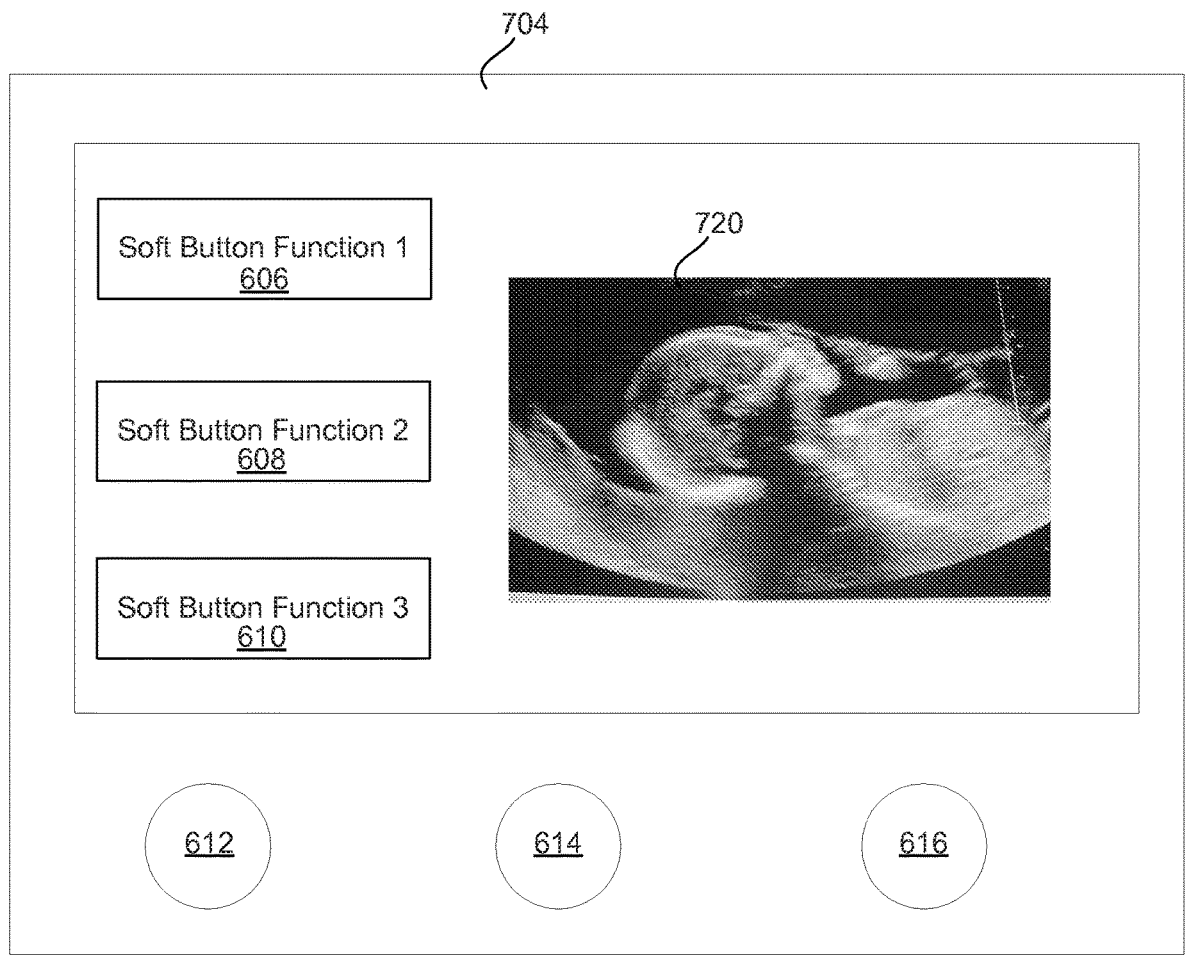
FIG. 7 illustrates a user interface of the portable defibrillator of FIG. 3 when operating in the ultrasound mode.

Referring now to FIG. 7, the ultrasound user interface 704 includes a parameter window 720 in which the ultrasound information, which may include physiological parameters as well as an ultrasound image, may be displayed. The ultrasound user interface 704 includes soft buttons 606-610, which are each associated with predetermined functions, such as zoom in/out, print, save, and the like.

Figure 8:
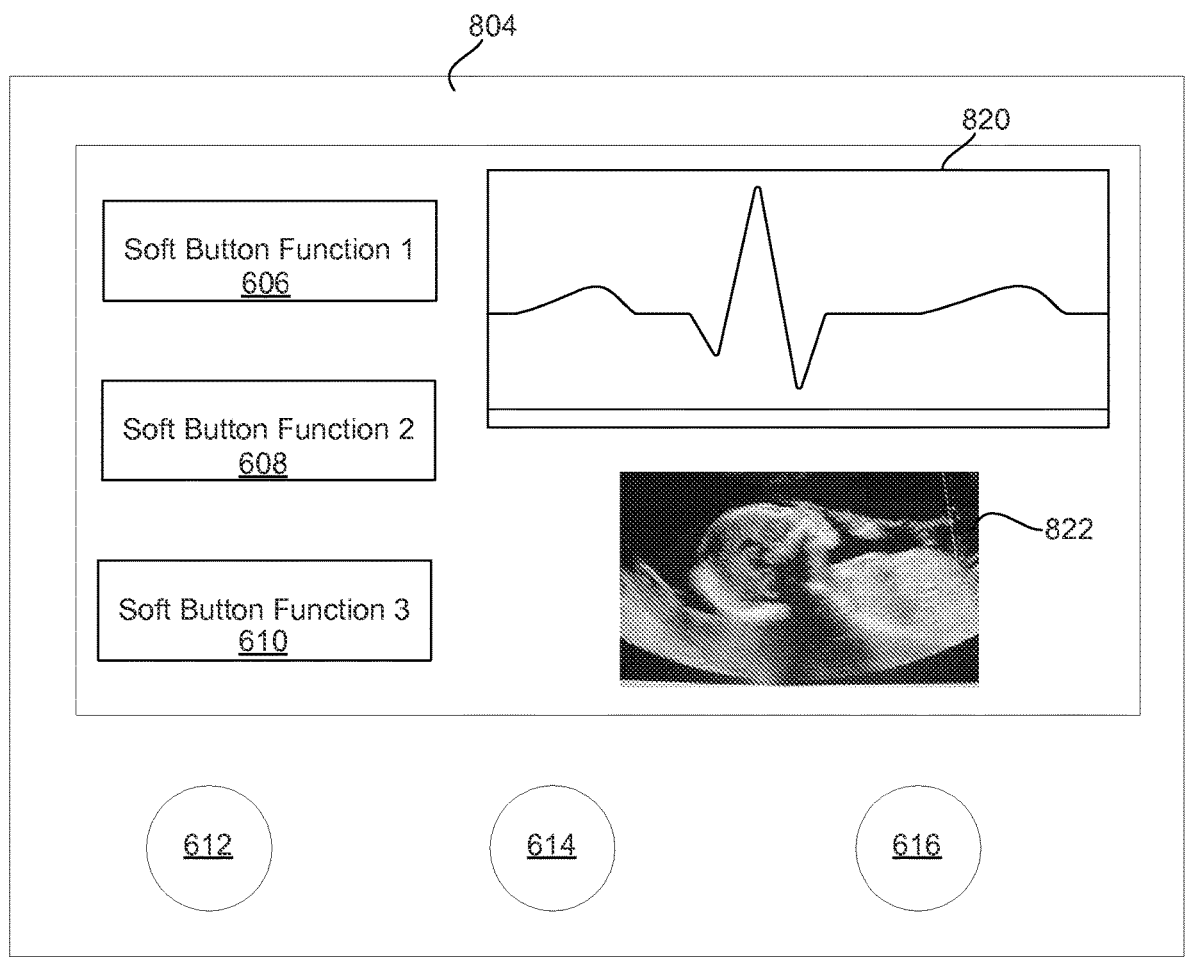
FIG. 8 illustrates a user interface of the portable defibrillator of FIG. 3 when operating in the joint display mode.

Referring now to FIG. 8, the joint user interface 804 includes two parameter windows 820, 822 in which information from a virtual machine host and a virtual machine may be simultaneously displayed. For example, as shown in FIG. 8, information from the defibrillator and the ultrasound virtual machine are both displayed. In FIG. 8, the windows 820, 822 are shown as vertically aligned but other configurations are also contemplated, such as horizontally aligned, overlapping, picture-in-picture, etc. In some embodiments, more than two windows may be used to display information from more virtual machines. In other embodiments, multiple windows may be used to display information from a single virtual machine. In some embodiments, the soft buttons 606-610 are used to close one or both of the parameter windows. In those scenarios, the virtual machine may enlarge the remaining window(s) to occupy the available space or may leave the windows unchanged until instructed by a paramedic.

Figure 9:
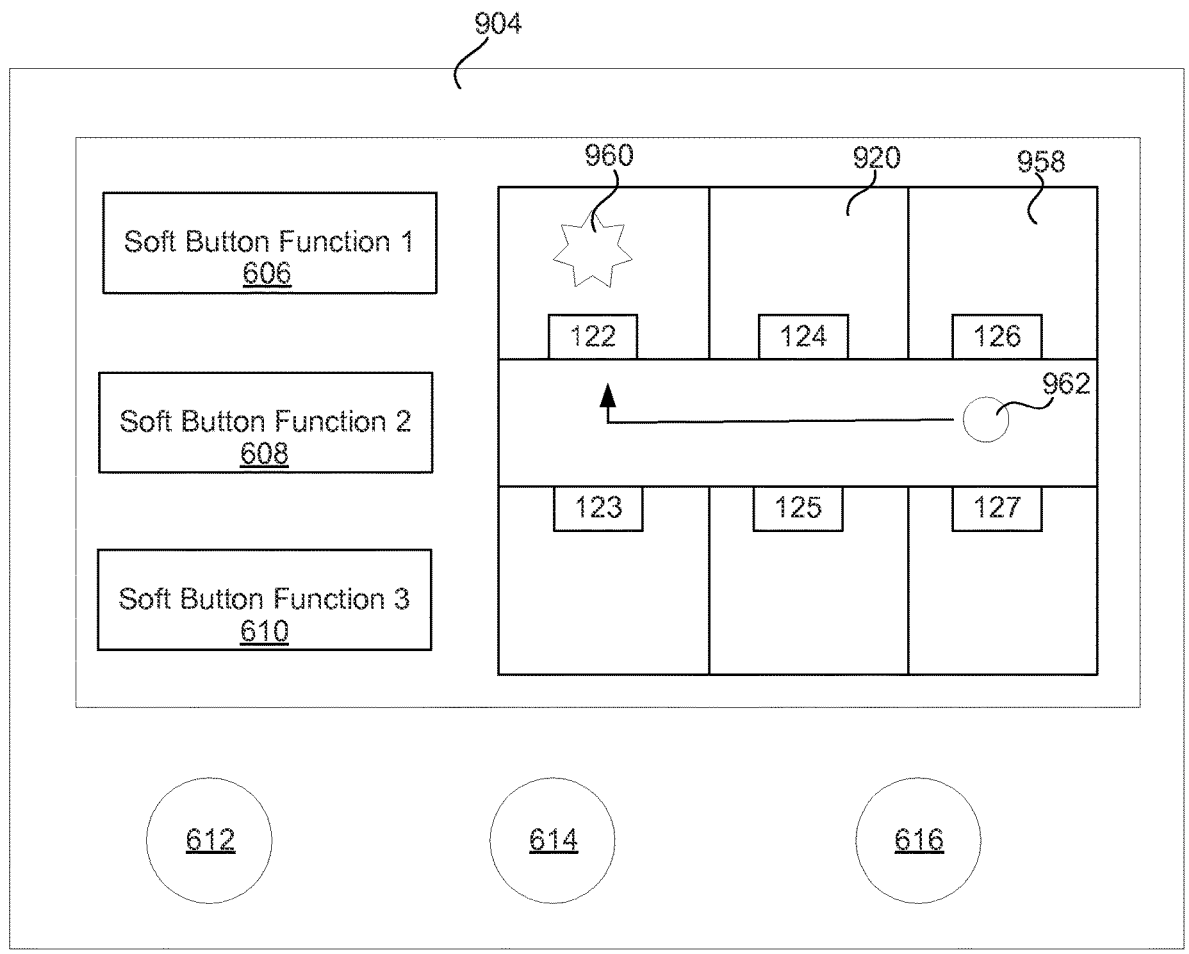
FIG. 9 illustrates a user interface of the portable defibrillator of FIG. 3 when operating in the GPS mode.

Referring now to FIG. 9, the GPS user interface 904 includes a window 920 in which GPS tracking information is shown. For example, user interface 904 depicts a map 958 showing the location 962 of the modified medical device 602 in relation to the location 960 of a reported emergency in an apartment building. Providing GPS tracking information helps a paramedic to quickly locate persons in distress, and including that functionality into a modified medical device 602, such as a portable defibrillator, enables paramedics to quickly access that information without requiring the use of additional equipment. The soft buttons 606-610 and/or the hard buttons 612-616 may be used to close the window 920 or change control to a different virtual machine. In some embodiments, the modified medical device 602 (e.g., via the virtual machine operating the GPS user interface 902) detects when the paramedic has arrived at the reported emergency (e.g., when the paramedic is within a predetermined distance from the emergency) and automatically transitions to a "home" medical device mode (e.g., a defibrillator mode). The modified medical device 602 may also detect when the paramedic is far from the reported emergency (e.g., when the paramedic is outside of a predetermined distance from the emergency) and automatically transitions to the GPS device mode.

Figure 10:
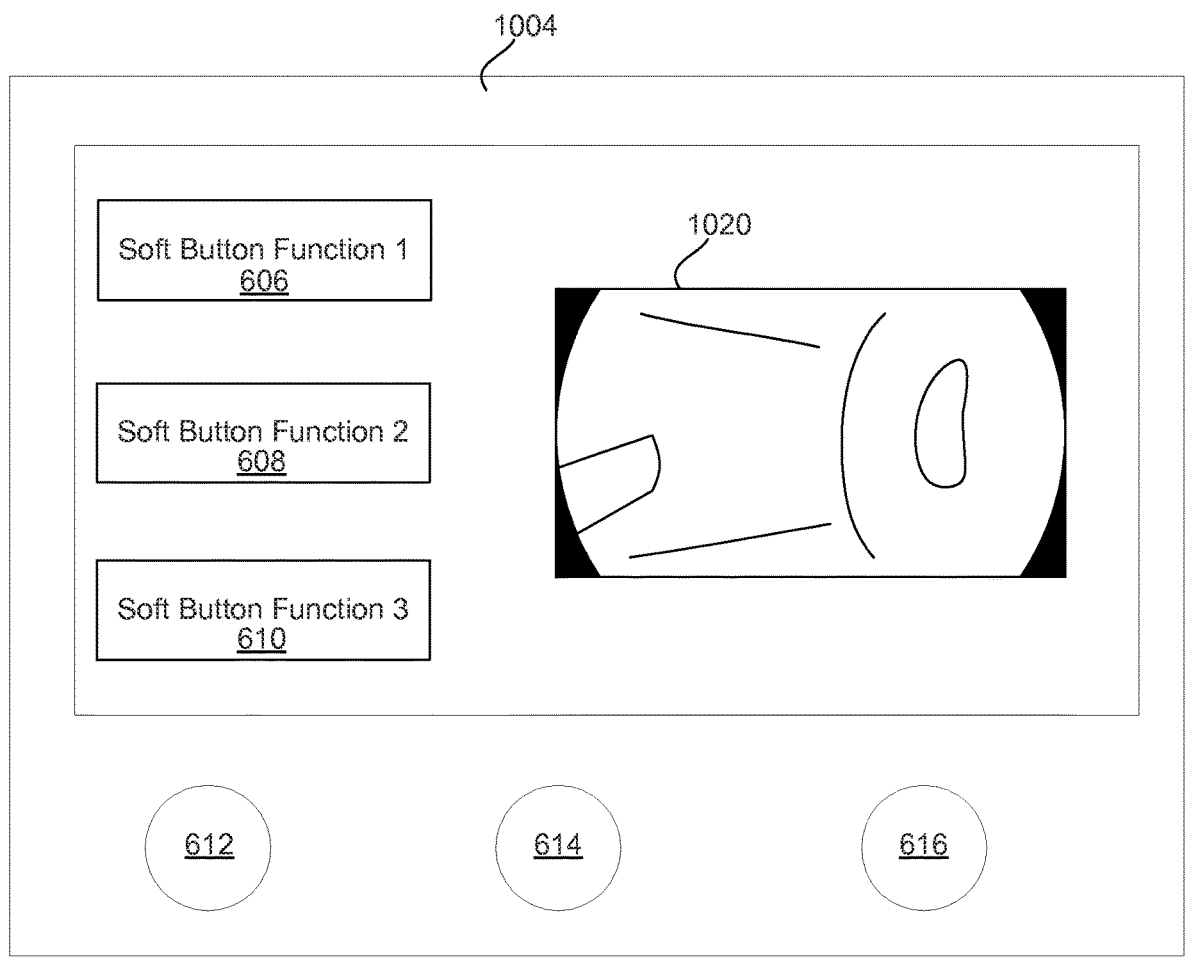
FIG. 10 illustrates a user interface of the portable defibrillator of FIG. 3 when operating in the endoscopy mode.

Referring now to FIG. 10, the endoscopy user interface 1004 includes a parameter window 1020 in which endoscopy information, which may include physiological parameters as well as an endoscope image, may be displayed. The endoscopy user interface 1004 includes soft buttons 606-610, which are each associated with predetermined functions, such as zoom in/out, print, save, and the like. The parameter window 1020 may also be displayed as part of a joint user interface that includes multiple parameter windows.

Figure 11:
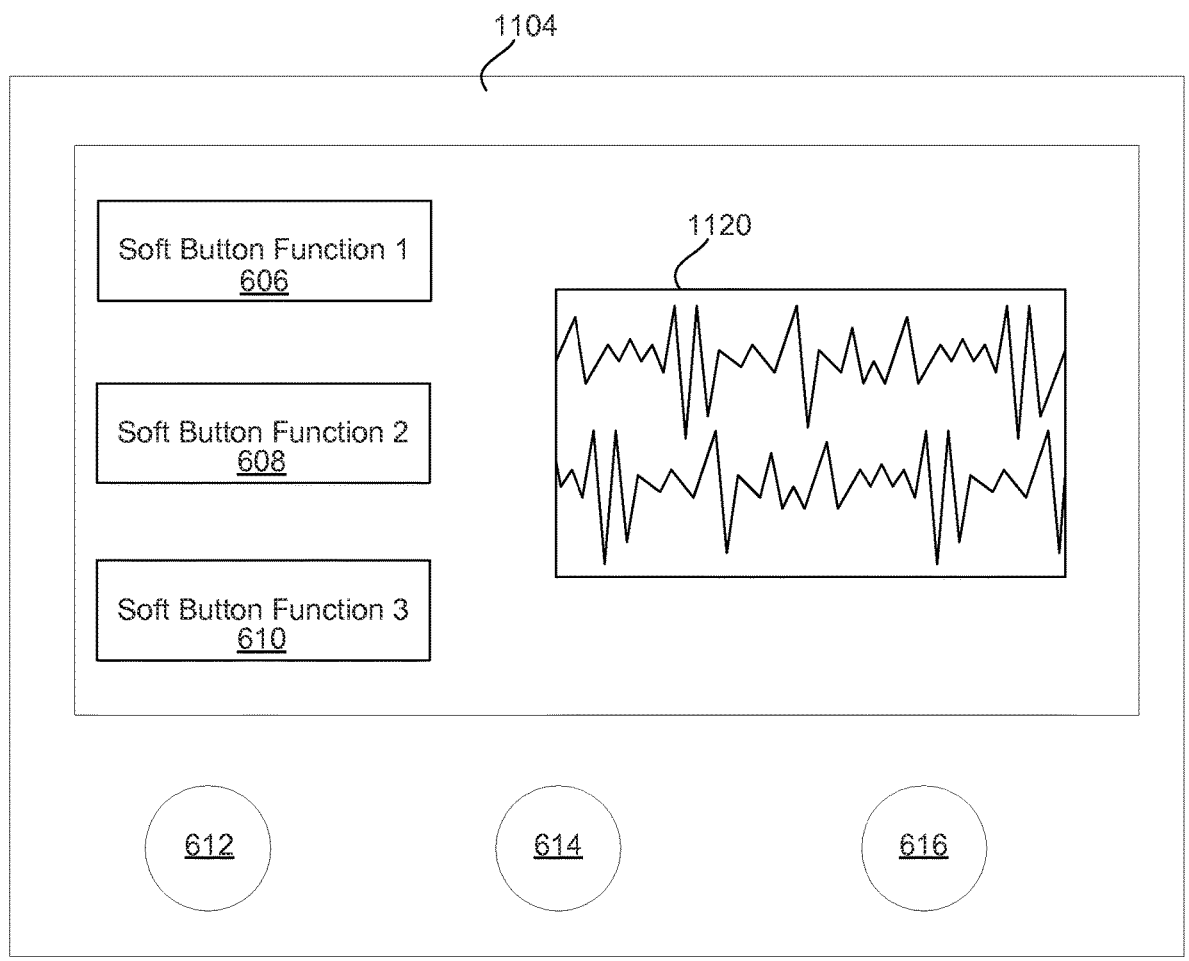
FIG. 11 illustrates a user interface of the portable defibrillator of FIG. 3 when operating in the EEG mode.

Referring now to FIG. 11, the EEG user interface 1104 includes a parameter window 1120 in which EEG information, which may include physiological parameters as well as a digital EEG stripchart, may be displayed. The EEG user interface 1104 includes soft buttons 606-610, which are each associated with predetermined functions, such as zoom in/out, print, save, and the like. The parameter window 1120 may also be displayed as part of a joint user interface that includes multiple parameter windows.

In some embodiments, a primary device or a virtual machine host may include a web server for connecting to secondary or "client" devices provided by third party manufacturers. The primary device may share resources with such secondary devices, such as display screens, printers, controls, wireless connections, and/or the like.

As described herein, a defibrillator, such as a portable defibrillator, may be configured to interface with other devices, for example medical devices. Such interface may be achieved via a web server hosted on the defibrillator, and a client browser or device on the peripheral device, according to some embodiments of the present invention. Such interface may be achieved with the defibrillator acting as a host for a virtual machine running on the defibrillator, with the virtual machine governing the interface of the peripheral device with the defibrillator. Because defibrillators often have independent display hardware, printing or hardcopy hardware, control hardware, and/or power source hardware, such hardware resources may be shared with peripheral medical devices as described above and according to embodiments of the present invention, in order to decrease the number of components and/or the bulk or weight of the peripheral device. This can be especially beneficial for paramedics who must carry portable medical equipment in emergency medical situations.

While many of the embodiments discussed above focus on sharing the screen of a primary device, other resources of the primary device may also be shared. For example, a portable defibrillator may be equipped with wireless communication capabilities to communicate over WLAN or cellular networks. In those embodiments, the secondary device may transmit its physiological information to the primary device, which can then transmit the physiological information to a remote location, such as a hospital. In some embodiments, the wireless capability of the primary device is used to project its user interface to the remote location, so that the remote location can monitor the physiological parameters tracked by the various medical devices at the scene of the emergency.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A shared resource medical system for monitoring a patient during emergency situations, the system comprising:
a primary medical device that is coupled to a user interface device, and that is configured to provide a displayed user interface at the user interface device, the primary medical device comprising:
a processor configured to wirelessly receive and transmit data;
at least one secondary medical device communicatively coupled to the primary medical device and configured to:
collect second physiological information from a patient; and
transmit the second physiological information to the primary medical device; and
a remote computing device disposed at a location remote from the primary medical device and the at least one secondary medical device,
wherein the primary medical device is configured to:
collect first physiological information from the patient,
receive the second physiological information from the at least one secondary medical device, and
transmit the second physiological information to the remote computing device,
wherein the remote computing device is configured to monitor the second physiological information collected by the at least one secondary medical device, and
wherein the displayed user interface is configured to
display the second physiological information,
replace the displayed second physiological information with the first physiological information in response to a detection by the primary medical device of a patient condition for which the first physiological information is more critical to patient care than the second physiological information.

2. The shared resource medical system of claim 1, wherein the remote computing device is disposed at a hospital.

3. The shared resource medical system of claim 1, wherein the user interface device comprises a touchscreen.

4. The shared resource medical system of claim 1, wherein the primary medical device is configured to project the displayed user interface to the remote computing device.

5. The shared resource medical system of claim 1, wherein the primary medical device is configured to:
store the first physiological information in a patient encounter record at a data storage device associated with the primary medical device, and
store the second physiological information in the patient encounter record.

6. The shared resource medical system of claim 1, wherein the primary medical device comprises one or more sensors configured to collect the first physiological information, wherein the one or more sensors comprise at least one of ECG sensors configured to collect ECG data or capnography sensors configured to collect capnography data.

7. The shared resource medical system of claim 1, wherein the primary medical device comprises a defibrillator.

8. The shared resource medical system of claim 7, wherein the defibrillator comprises one or more defibrillator sensors comprising ECG leads configured to obtain ECG data, and wherein the defibrillator comprises at least one defibrillator processor configured to receive and process the ECG data to generate an ECG waveform.

9. The shared resource medical system of claim 8, wherein the at least one defibrillator processor is configured to control a display screen to simultaneously display the ECG waveform and other defibrillator information.

10. The shared resource medical system of claim 1, wherein the primary medical device is configured to monitor alarm conditions of the at least one secondary medical device.

11. The shared resource medical system of claim 1, wherein the at least one secondary medical device comprises at least one of a ventilator, an oximeter, or a blood pressure monitor.

12. The shared resource medical system of claim 1, wherein the at least one secondary medical device comprises an ultrasound transducer.

13. The shared resource medical system of claim 1, wherein the at least one secondary medical device comprises at least one of an endoscope or electroencephalography sensors.

14. The shared resource medical system of claim 1, wherein the primary medical device is coupled to global positioning system (GPS) circuitry and is configured to provide GPS tracking information.

15. The shared resource medical system of claim 1, wherein the processor is configured to wirelessly receive and transmit data via one or more of a wireless local area network (WLAN) and a cellular network.

16. The shared resource medical system of claim 1, wherein the at least one secondary medical device is communicatively coupled to an ultrasound transducer.

17. The shared resource medical system of claim 16, wherein the at least one secondary medical device comprises a user interface configured to display ultrasound information.

18. The shared resource medical system of claim 1, wherein the primary medical device is configured to store the first physiological information in a patient encounter record at a data storage device associated with the primary medical device.

19. The shared resource medical system of claim 1, wherein the primary medical device comprises one or more sensors configured to collect the first physiological information.

20. The shared resource medical system of claim 1, wherein the primary medical device is configured to store the second physiological information in a patent encounter record at a data storage device associated with the primary medical device.

* * * * *